(12) United States Patent
Milton et al.

(10) Patent No.: US 8,411,266 B2
(45) Date of Patent: Apr. 2, 2013

(54) MEASUREMENT OF PARTICLES IN LIQUID USING REFLECTED LIGHT

(75) Inventors: Sven Milton, Vikingstad (SE); Paolo Massarutti, Brescia (IT)

(73) Assignee: Medical Vision Research & Development AB, Nacka (SE)

(*) Notice: Subject to any disclaimer, the term of this patent is extended or adjusted under 35 U.S.C. 154(b) by 345 days.

(21) Appl. No.: 12/736,371

(22) PCT Filed: Mar. 23, 2009

(86) PCT No.: PCT/SE2009/050301
§ 371 (c)(1),
(2), (4) Date: Oct. 26, 2010

(87) PCT Pub. No.: WO2009/123547
PCT Pub. Date: Oct. 8, 2009

(65) Prior Publication Data
US 2011/0051136 A1      Mar. 3, 2011

(30) Foreign Application Priority Data
Apr. 4, 2008   (SE) .................................. 200800762

(51) Int. Cl.
*G01N 21/00* (2006.01)
*G01N 21/90* (2006.01)

(52) U.S. Cl. ............... 356/246; 356/239.6; 356/427; 356/445

(58) Field of Classification Search .............. 356/244, 356/246, 338, 337, 335, 336, 39, 445
See application file for complete search history.

(56) References Cited

U.S. PATENT DOCUMENTS

| | | | |
|---|---|---|---|
| 5,726,751 A * | 3/1998 | Altendorf et al. | 356/246 |
| 6,511,454 B1 | 1/2003 | Nakao et al. | |
| 6,537,356 B1 * | 3/2003 | Soriano | 96/155 |
| 6,962,488 B2 | 11/2005 | Davis et al. | |
| 8,179,528 B2 * | 5/2012 | De Vries et al. | 356/338 |
| 2007/0249993 A1 * | 10/2007 | Mollstam et al. | 604/65 |
| 2010/0310423 A1 * | 12/2010 | Nieuwenhuis | 422/82.05 |

FOREIGN PATENT DOCUMENTS

| | | |
|---|---|---|
| EP | 0 319 278 B1 | 8/1992 |
| EP | 0 362 822 B1 | 1/1998 |
| WO | WO 2007/044548 A3 | 4/2007 |

* cited by examiner

*Primary Examiner* — Layla Lauchman
*Assistant Examiner* — Cecily Smith
(74) *Attorney, Agent, or Firm* — Renner, Otto, Boisselle & Sklar, LLP

(57) ABSTRACT

An improved cassette for detecting and quantifying particles in a liquid is provided. A sample volume of a liquid is held by a housing with an inlet and an outlet for the liquid. Light is emitted across the sample volume and reflected creating a doubled length of the optical path in the sample volume. The probability of detecting particles is increased and the measurement is improved. The housing reduces noise due to air bubbles and improves sensitivity of detection of particles in the liquid sample.

9 Claims, 4 Drawing Sheets

MEASUREMENT OF PARTICLES IN LIQUID USING REFLECTED LIGHT

CROSS-REFERENCE TO RELATED APPLICATIONS

This application claims priority from International Patent Application No. PCT/SE2009/050301 filed Mar. 23, 2009, claiming priority from Swedish Application SN SE 0800762-7 filed Apr. 4, 2008.

FIELD OF THE INVENTION

The present invention relates to the measurement of particles in a liquid using reflected light generally and detection and measurement of biological material in a housing for a sample volume of fluid that is aspirated from a surgical site during Endoscopic procedures specifically.

BACKGROUND OF THE INVENTION

During Endoscopic surgical procedures, a surgical site such as a knee joint, shoulder joint or other cavity in the body of a human or animal is viewed with an endoscope. Further in this document, the surgical site for an Endoscopic procedure is referred to as the body cavity. The body cavity is irrigated with a clear liquid in order to expand it, improve the view of it and to rinse the cavity. The irrigation is achieved by means of a pump. This pump is further in this document referred to as an inflow liquid pump. The clear liquid is as a rule saline, and the pump is usually a peristaltic roller type pump. Also, the surgical procedures normally involve the removal of, or work on tissue, for instance the meniscus of the knee. This results in debris, namely particles of various sizes of tissue floating around in the liquid in the body cavity. These particles are routinely removed by rinsing. To rinse out blood and/or debris, the liquid in the body cavity is replaced by introducing or increasing liquid flow through the body cavity. The outflow of the irrigation liquid is normally transported via a tubing to a waste bucket.

Existing liquid management systems are either operated by a fixed flushing flow selected by the operator of the system when starting the procedure, or by a fixed pressure target for the system.

Cassettes for peristaltic pumps and similar medical applications have been developed in order to create and improve the handling of the tubing and flow of liquid. EP0362822 B1 "Disposable vacuum/peristaltic pump cassette system" describes a disposable cassette and U.S. Pat. No. 6,962,488 B2 "Surgical cassette having an aspiration pressure sensor" discloses a cassette system used for eye surgery and design with channels for the fluid based on hard and soft plastic.

Detection of blood and debris in outflow tubing is previously discussed in WO 2007/114776 "Method and device for irrigation of body cavities" disclosing a method and apparatus for detecting biological material such as blood and debris in an irrigation fluid from a body cavity. The outflow liquid device detecting biological material consists of light emitting diodes (LED) and optical sensors for hemoglobin, debris and optionally a calibrating detector mounted on the tubing. The described optical detector is fitted on the housing for the pump system, but may optionally be fitted near or even directly by or within the surgical instrumentation that is forming the liquid path emerging from the patient, such as a shaver tool or cannula. The described optical light emitting and sensor arrangement forms an optical path in the liquid in the housing of a vessel in the liquid outflow path of the irrigation fluid.

The detection of particles and methods to analyze fluids such as body fluids are is well known within the area of dialysis. WO2007044548 "fluid handling system" discusses a cassette system for analyzing body fluids for determining the concentration of analyte in a sample. A patient cassette system with functions such as sensors for hemoglobin and optical or ultrasonic "bubble sensors" indicate the presence of air in the liquid pathway. Furthermore, since it is crucial not to infuse air into blood systems, methods are used to indicate air bubbles connected to a warning system. U.S. Pat. No. 6,511,454 B1 "irrigation/aspiration apparatus and irrigation/aspiration cassette" discloses such a system. And EP319278B1 "Disposable cassette for a medication infusion system" teaches a design for removal of air bubbles.

While existing products for dialysis and medical liquid inflow systems may be suitable for the particular purpose to which they address, they are not as suitable for optical measurement of diluted particles in for example aspirated fluid.

Optical measurement of particles such as body fluids in a sample in a liquid such as irrigation fluid is highly dependent on the housing of the sample volume and the implementation of the measurement system. The optical path needs to be long enough in order to detect low numbers of particles. Noise from for example air bubbles and unnecessary differences in optical refraction along the optical path should be avoided and the housing of the sample volume should be stable and easily mounted to the optical sensors. The wording "sample volume" refers to, and will hereinafter be referred to, the liquid in the optical path in the liquid in the housing.

In these respects, the detection of particles and design of housing of the sample volume according to the present invention substantially departs from the conventional concepts and designs of the prior art, and in doing so provides products primarily developed for the purpose of an improved measurement of particles such as blood and debris in a sample volume such as that in a cassette system for aspirated irrigation fluid.

SUMMARY OF THE INVENTION

The general purpose of the present invention, which will be described subsequently in greater detail, is to provide an improved and more sensitive detection of particles in a sample volume (the volume of liquid in a housing where the detection occurs) such as in irrigation fluid from a body site and a cassette for the housing of the sample volume of aspirated irrigation fluid that have many advantages concerning improved detection of blood, debris and removal of noise such as air either alone or in any combination thereof.

To attain this, the present invention generally comprises a cassette mounted on a peristaltic pump that contains a housing for a sample volume of aspirated irrigation fluid. The housing is characterized by a reflection area on one side of the housing reflecting optical signals through the sample volume.

There has thus been outlined, rather broadly, the more important features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide for an improved detection of blood cells, red blood cells, hemoglobin and/or debris in a sample volume of irrigation fluid aspirated from a surgical site, through reflecting an optical signal on a reflecting area of the housing of the cassette encompassing a sample volume.

Another object of the present invention is to provide for a cassette used on peristaltic pump containing a housing for a sample volume for aspirated irrigation fluid with a reflector on the opposite to the pump mounting area.

Other objects and advantages of the present invention will become obvious to the reader and it is intended that these objects and advantages are within the scope of the present invention.

DETAILED DESCRIPTION OF THE INVENTION AND PREFERRED EMBODIMENTS THEREOF

The invention relates to a cassette containing a housing for holding a sample volume of irrigation fluid, characterized in that it is made of a transparent material and has at least one inlet opening and at least one outlet opening and by having at least one reflection area on at least one side of the housing reflecting optical signals through the sample volume in an optical path.

In one embodiment the length of the optical path is multiplied one or more (n) times by one or more (n) reflecting areas, wherein n is an integer of at least 1. The number of reflecting areas may be even or uneven.

The optical signals may emerge from at least one light emitting device and reach at least one optical sensor. These may be placed on the same side of the sample volume. Thus, according to one embodiment the number of reflecting areas and the placement thereof are chosen so that the light reaches the optical sensor on the same side of the sample volume as the light emitting device is placed.

An improved and more sensitive detection of particles in a sample volume such as irrigation fluid from a body cavity is obtained by a reflection of the measured light creating a doubled length of the optical path. This also results in the possibility of having sensitive parts such as light emitting diodes and optical sensors on the same side of the sample volume and a smaller width or height of the sample volume.

In the case of applying the sample volume in a housing of a cassette used for irrigation fluid, the system has many advantages concerning improved detection of blood and/or debris. The system (explained more in detail in example 1) has an improved sensitivity to differentiate between different types of particles and solutions in the sample volume. This is important since the optical path is longer and the likeliness of particles crossing the optical path increases in relation to the length of the optical path in the solution.

The advantages of the invention described herein are especially evident in the case of detecting blood and debris in a sample volume of irrigation fluid. The extent of each content component and differentiation between whether there is a certain amount of blood or a certain amount of debris can be measured. This can for example improve the control of a peristaltic pump based on the existence of blood and/or debris.

Figure 1:
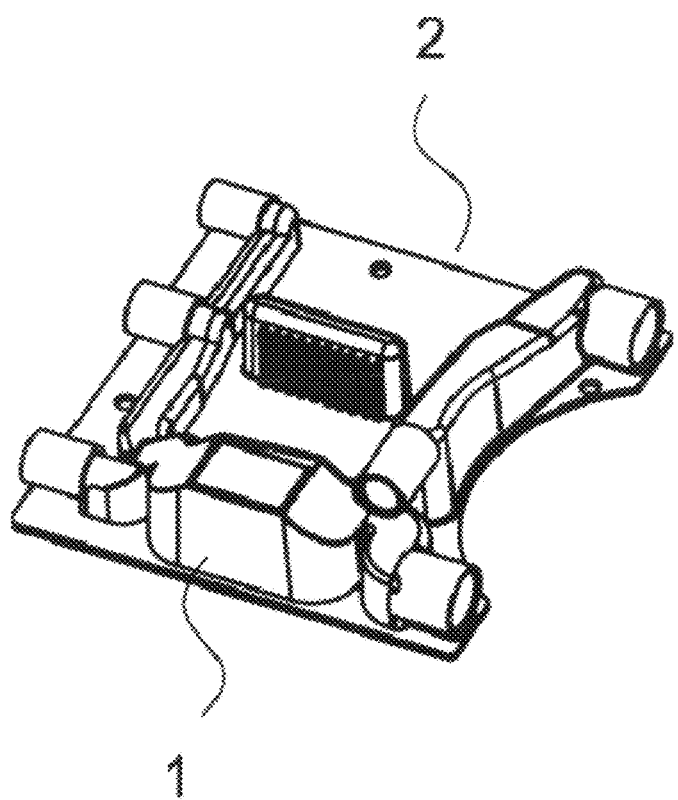
FIG. 1: Example of design for a cassette used on a peristaltic pump.
Figure 2:
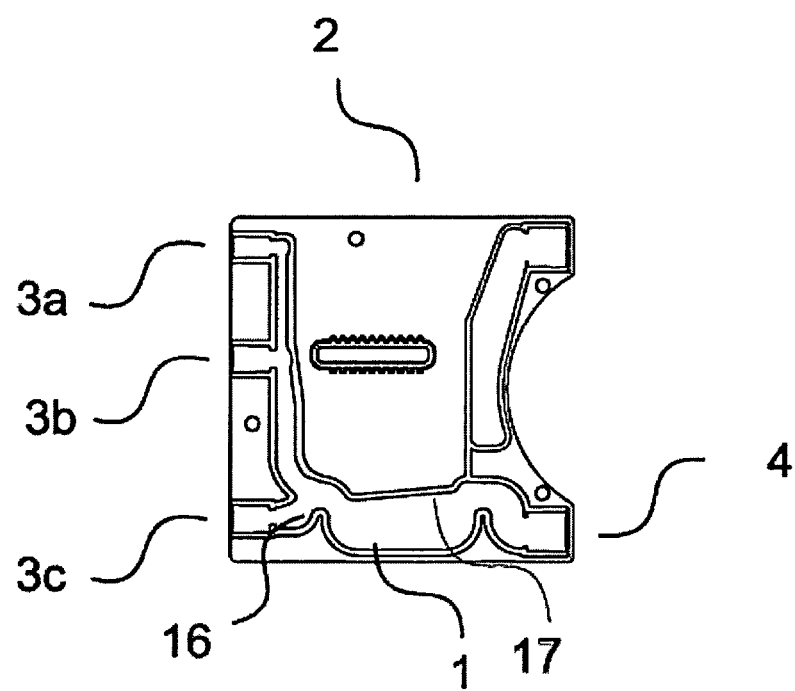
FIG. 2: A cassette showing the design of housing for a sample volume and connections to tubes.
Figure 3:
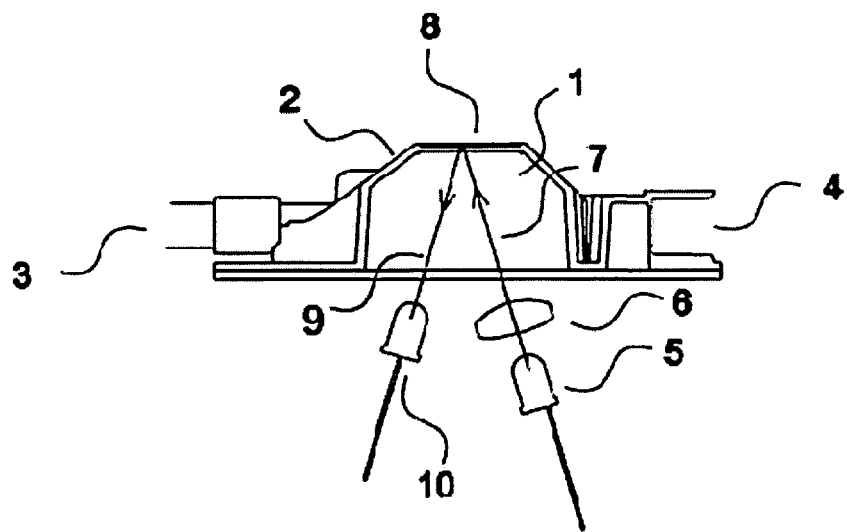
FIG. 3: A cassette showing an optical path.
Figure 4:
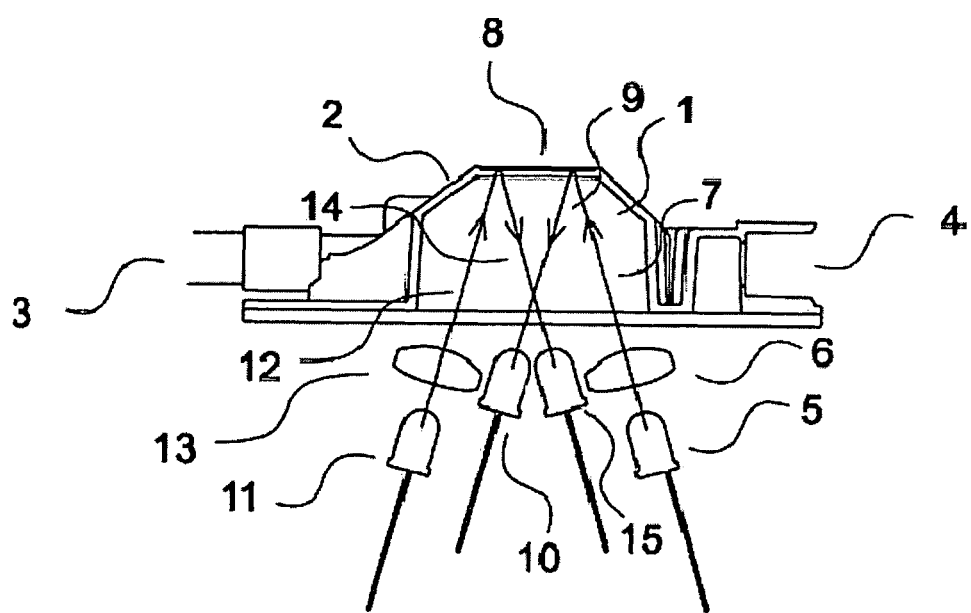
FIG. 4: A design of a cassette showing two optical paths.

In order to attain an improved detection of particles, the housing for the sample volume can be designed to prevent noise such as air bubbles and improve the chances of detecting particles such as debris. The noise from air bubbles can be reduced by creating a "pool of liquid" for the sample volume creating space for the air on top of the pool. The pool can either be created by lowering the housing of the sample volume (1) in relation to the inlet (3) and outlet (4) or by ridges (16) forcing the air bubbles to the top of the housing as shown in FIG. 2. Furthermore, the housing can be designed to automatically lead away the air. This can for example be achieved by a sloping of the top (17) or "roof" of the housing as shown in FIG. 2.

Apart from improving the detection by reflecting light the chances of detecting particles such as debris in a sample volume can be improved by creating turbulence in the sample volume and thus improving the chances for the particles (of different size and weight) to pass the optical detection path. This can for example be created by the above mentioned ridges (16) of the sample volume (1) shown in FIG. 2.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

EXAMPLE 1

An example of the described cassette follows:

During arthroscopic procedures, the joint of a patient is distended with irrigation liquid. This liquid is sterile saline irrigated by a pump for the purpose. A second pump has the feature to remove—or aspirate—the liquid from the joint. Surgical work is performed with manual or powered tools to the joint. The surgeons work may result in bleeding as blood vessels rupture as a consequence of the work. The usage of tools also results in fragments of cartilage or bone tissue of varying sizes floating around in the liquid in the joint. Both the fragments and the blood are distracting for the viewer of the view in the arthroscope and are aspirated from the joint by the aspiration pump. The liquid is aspirated from the patient either through the surgical tool or via an outflow port from the patient's joint. The aspiration pump is of the volumetric roller pump type, and thus has flexible tubing as part of the pump system. This flexible tubing is connected to a cassette.

This cassette is made of transparent material letting light pass through such as polycarbonate. It has a housing or compartment (1) as part of the liquid pathway from the joint to the tubing of the aspiration pump. The cassette has a frame structure (2). The cassette has inputs (3) from surgical instruments or outflow port, and connections to the aspiration pump tubing segment (4). The compartment (1) has a shape to beneficially contain a sample volume of the aspirated liquid for the purpose of irrigation of light through this sample volume (1). The cassette is fitted on the housing of the aspiration pump. Adjacent to the cassette a light emitting diode (5) is fitted. The emission wavelength is 880 nm. The light beam is converted by the convex lens (6), and is passing through the wall of the cassette structure encompassing the sample volume (1). As the light beam (7) travels through the sample volume (1) of the aspirated liquid, its intensity is reduced as a result of scattering and absorption by fragments of cartilage tissue or bone tissue in the aspirated liquid. The light beam is then reflected by the reflective surface (8), and travels once more through the sample volume (1). The intensity is further reduced by fragments as the traveled distance of the light beam (9) is doubled in the sample volume (1). Finally the light intensity is detected by the light sensitive diode (10). The aspiration pump speed is controlled by the signal from the light sensitive diode (10)).

EXAMPLE 2

This example shows an enhancement of detection of blood in the cassette, a second light emitting diode (11) is fitted adjacent to the cassette. The wavelength is in this case 370 nm. The light beam (12) is converted by the convex lens (13), and then travels through the sample volume (1) of the aspirated liquid. Its intensity is reduced as a result of scattering and absorption by the blood in the aspirated liquid. The light beam is then reflected by the reflective surface (8), and travels once more through the sample volume (1). The intensity is further reduced by blood as the traveled distance of the light beam (14) is doubled in the sample volume (1). Finally the light intensity is detected by the light sensitive diode (15). The difference is signal intensities from the light sensitive diodes (10 and 15) is conceives a most sensitive detection of blood.

The invention claimed is:

1. A cassette for use in detection of particles in a sample volume of aspirated fluid comprising:

a housing for holding the sample volume, characterized in that is made of transparent material, said housing comprising at least one inlet opening and at least one outlet opening, and at least one means for forcing air bubbles in the sample volume to the top of said housing, said housing further comprising one reflection area on at least one side of the housing thereby reflecting optical signals through the sample volume in an optical path; the housing being configured to create a space of air on top of a pool of liquid of the sample volume.

2. The cassette according to claim 1 wherein the length of the optical path is multiplied n times by n reflecting areas, wherein n is an integer of at least 1.

3. The cassette according to claim 1, wherein said optical signals emerge from at least one light emitting device and reaches at least one optical sensor.

4. The cassette according to claim 3 wherein the at least one light emitting device and the at least one optical sensor are placed on the same side of the sample volume for improving the sensitivity of the detection by increasing the optical path in the sample volume.

5. The cassette of claim 1 wherein the space of air on top of the pool of liquid of the sample volume is created by means of mounting a slope in the upper part of the housing.

6. The cassette of claim 1 wherein the space of air on top of the pool of liquid of the sample volume is created by means of placing the inlet opening and outlet opening in the upper part of the housing.

7. The cassette of claim 1 wherein the said means for forcing air bubbles in the sample volume to the top of the housing comprises one or more ridges.

8. The cassette of claim 7 wherein the ridges are placed near the inlet of the housing.

9. The cassette according to claim 7 wherein the ridges can further create turbulence thereby improving the chances for particles to pass the optical path.

* * * * *

UNITED STATES PATENT AND TRADEMARK OFFICE
CERTIFICATE OF CORRECTION

PATENT NO.       : 8,411,266 B2                                                              Page 1 of 1
APPLICATION NO.  : 12/736371
DATED            : April 2, 2013
INVENTOR(S)      : Milton et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 367 days.

Signed and Sealed this
First Day of September, 2015

Michelle K. Lee
*Director of the United States Patent and Trademark Office*